(12) United States Patent
Mikedis

(10) Patent No.: US 10,139,315 B2
(45) Date of Patent: Nov. 27, 2018

(54) TABLET SAMPLER ASSEMBLY

(71) Applicant: Bosch Packaging Technology Limited, Merseyside (GB)

(72) Inventor: Simos Mikedis, Liverpool (GB)

( * ) Notice: Subject to any disclaimer, the term of this patent is extended or adjusted under 35 U.S.C. 154(b) by 200 days.

(21) Appl. No.: 15/033,795

(22) PCT Filed: Nov. 3, 2014

(86) PCT No.: PCT/GB2014/053266
§ 371 (c)(1),
(2) Date: May 2, 2016

(87) PCT Pub. No.: WO2015/063517
PCT Pub. Date: May 7, 2015

(65) Prior Publication Data
US 2016/0252433 A1 Sep. 1, 2016

(30) Foreign Application Priority Data

Nov. 1, 2013 (WO) ................ PCT/GB2013/052871

(51) Int. Cl.
*G01N 1/04* (2006.01)
*A61J 3/00* (2006.01)
(Continued)

(52) U.S. Cl.
CPC ................ *G01N 1/04* (2013.01); *A61J 3/005* (2013.01); *G01N 1/2035* (2013.01); *A61J 3/10* (2013.01);
(Continued)

(58) Field of Classification Search
None
See application file for complete search history.

(56) References Cited

U.S. PATENT DOCUMENTS 2,849,965 A * 9/1958 Stott ...................... B30B 11/34
425/112
3,881,356 A * 5/1975 Palm ...................... G01N 1/04
73/863.91
(Continued)

FOREIGN PATENT DOCUMENTS

CA 383719 10/1971
JP S6137244 A 2/1986
(Continued)

OTHER PUBLICATIONS

International Search Report and Written Opinion for Application No. PCT/GB2014/053266 dated Dec. 4, 2014 (3 pages).

*Primary Examiner* — Jill E Culler
(74) *Attorney, Agent, or Firm* — Michael Best & Friedrich LLP

(57) ABSTRACT

A tablet sampler assembly is provided for a tablet coating machine which comprises a rotatable drum for containing a bed of tablets being coated. The tablet sampler assembly comprises a housing configured for attachment to said tablet coating machine, and a receptacle for receiving a sample of said tablets. At least a portion of the receptacle is movable between a collecting position in which the receptacle is configured to be in communication with the interior of the drum, thereby enabling collection of a sample by the receptacle from the drum, and a non-collecting position in which the receptacle is configured to be substantially out of communication with the interior of the drum.

12 Claims, 14 Drawing Sheets

(51) Int. Cl.
  *G01N 1/20*    (2006.01)
  *A61J 3/10*    (2006.01)
  *B30B 11/34*   (2006.01)
  *G01N 1/08*    (2006.01)

(52) U.S. Cl.
  CPC ........ *B30B 11/34* (2013.01); *G01N 2001/085* (2013.01)

(56) References Cited

U.S. PATENT DOCUMENTS

| | | | | |
|---|---|---|---|---|
| 4,640,376 A | * | 2/1987 | Hinzpeter | G01G 17/00 177/50 |
| 5,905,213 A | * | 5/1999 | Jaeger | G01N 1/2035 73/863.85 |
| 6,843,103 B2 | * | 1/2005 | Aguilera | G01F 1/74 73/28.01 |
| 7,363,830 B2 | * | 4/2008 | Girard | G01N 1/14 73/863.42 |
| 2013/0104673 A1 | * | 5/2013 | Isobe | G01N 1/08 73/863.01 |

FOREIGN PATENT DOCUMENTS

| | | |
|---|---|---|
| JP | 11316222 | 11/1999 |
| WO | 2010071964 | 7/2010 |

\* cited by examiner

TABLET SAMPLER ASSEMBLY

BACKGROUND OF THE INVENTION

The present invention relates to a tablet sampler assembly of the kind that may be used to extract tablet samples from a tablet coating machine.

Tablet coating machines are used in the pharmaceutical industry to apply a coating to medicament tablets. For instance, tablets with an unpleasant taste may be coated with a sweet-tasting coating, such as a sucrose-based coating, so as to make them more palatable and thus more comfortable to swallow. As another example, tablets may be coated with a substance containing an active drug in order to target the release of the active pharmaceutical ingredient in, for example, the lower intestinal tract. Conventional coating machines comprise a circular drum defined by a circumferential peripheral wall and two frustoconical end walls. One or both of these end walls have apertures through which the drum can be loaded or unloaded. The drum is filled with a bed of tablets to be coated, and then rotated about its axis. As the drum rotates, the coating material is applied (commonly being sprayed from one or more spray guns positioned within the drum). Rotation of the drum agitates and mixes the bed of tablets, thereby evenly distributing the coating material into a layer which encompasses each of the tablets.

The peripheral wall of the drum is often porous (for instance being semi-perforated or fully perforated). In such cases the drum is often located within a housing to which warm air is supplied, and an open face of a plenum (also known as a suction shoe) is mounted in the housing at the point where the tablet bed lies while the drum is rotating. As the drum rotates, suction from the plenum sequentially draws warm air into the drum from the housing (through the porous peripheral wall of the drum), and from the drum through the tablet bed. Warm air passing through the tablet bed dries the coating on each of the tablets.

It is desirable to take samples of the tablet bed at one or more selected intervals during the coating process, for instance to inspect the evenness of the coating and the thickness of the coating layer. However, it is important that the drum rotates continuously throughout the coating process so that the tablet bed is continuously mixed, ensuring an even coat and preventing the coating material from sticking the tablets to one another. Sampling must therefore take place whilst the drum is in motion. Conventionally, sampling is performed by an operator reaching into the drum as it rotates and scooping out the required quantity of tablets. Such a practice is, however, inherently dangerous, particularly since coating machines often have drums with mixing baffles to assist with agitation of the tablet bed, and/or unloading blades to assist with emptying of the drum after the coating process is complete, and these can impact or trap body parts or clothing, potentially leading to operator injury.

One known coating machine addresses this problem by including a hose which projects into the drum and allows a sample from the tablet bed to be removed by suction through the hose due to the negative vacuum pressure applied. Though such a proposition may reduce the risk of operator injury, the generation of the vacuum pressure is and noisy, and adds additional bulk to the machine. In addition, in many pharmaceutical coating operations it is imperative that there is no opportunity for egress of coating material or tablet matter (such as dust given off by the tablet bed). The air with which the tablets are suctioned through the hose must therefore be filtered, further increasing the complexity and bulk of the machine. Furthermore, the hose obstructs the flow of warm air, the movement of the tablet bed and the spray of coating material from the spray guns, adversely affecting the evenness of the coating. Tablets may also collide with the pipe with sufficient force to break them.

SUMMARY OF THE INVENTION

It is therefore an object of the present invention to at least mitigate, and preferably to obviate, one or more of the aforesaid disadvantages, and/or to provide an improved or alternative tablet sampler assembly, tablet coating machine, method of collecting a sample and/or method of coating tablets.

According to a first aspect of the present invention there is provided a tablet sampler assembly for a tablet coating machine, the tablet coating machine comprising a rotatable drum for containing a bed of tablets being coated, the tablet sampler assembly comprising: a housing configured for attachment to said tablet coating machine, and a receptacle for receiving a sample of said tablets, wherein at least a portion of the receptacle is movable between a collecting position in which the receptacle is configured to be in communication with the interior of the drum, thereby enabling collection of a sample by the receptacle from the drum, and a non-collecting position in which the receptacle is configured to be substantially out of communication with the interior of the drum.

Utilization of a receptacle, at least a portion of which can be moved into and out of communication with the interior of the drum of a coating machine may provide a mechanism for extracting a sample from that drum which is safer than certain known methods in that it does not require an operator to reach into the drum whilst it is rotating. In addition, the at least a portion of the receptacle being movable out of communication with the drum may allow it to have a reduced effect on the movement of warm air, the tablet bed and the spray of coating material within the drum, improving the uniformity of the coating layer on the tablets and reducing the risk of breakage.

The housing may be a single-part or multi-part shell structure, a framework, or it may take any other suitable form. The housing may be configured to be attached to a coating machine so as to sealingly engage therewith, thus maintaining a contained environment. The receptacle may take any suitable form, such as a dish, platform, cup or bottle. It may define a volume for storage of a plurality of tablets. The plurality may be substantially the same number as the desired sample size, for instance 5-15 tablets. The receptacle may be positionable internally and/or externally of the housing.

The housing may comprise an outlet port through which the sample can be removed from the receptacle.

The housing and receptacle may be arranged to allow the sample to be removed from the receptacle, through the outlet port, under gravity. This may provide a mechanism for removal of the sample from the tablet sampler assembly which is advantageously simple. For instance, it allows samples to be taken without the need for vacuum pressure, allowing the sampler assembly to be smaller, simpler and/or quieter.

In one example of such an arrangement, the receptacle may be positionable above the outlet port, when the assembly is in position on a tablet coating machine, and the housing may define a chute for guiding tablets falling from the receptacle towards the outlet port. The receptacle may be positionable directly above the outlet port in which case the chute would be arranged vertically.

As an alternative, the tablet sampler assembly may be arranged to allow removal of the sample from the receptacle by other means, for instance the sample may be removed by lifting them by hand through a top port.

The housing and receptacle may be arranged to allow the sample to be removed from the receptacle through the outlet port when said portion of the receptacle is in the non-collecting position.

Movement of said portion to the non-collecting position may move the sample to outside the drum, allowing the tablets to be collected without the need for a more complex, bulky and/or noisy mechanism, such as a vacuum pressure system.

In such an arrangement, the sample may or may not be removable from the receptacle when said portion is in the non-collecting position. Alternatively, the housing and receptacle may be arranged to allow the sample to be removed from the receptacle through the outlet port when said portion is in the collecting position but not when in the non-collecting position.

The receptacle may be configured to project into the drum when said portion thereof is in the collecting position, and configured to project into the drum to a lesser extent, or not at all, when said portion is in the non-collecting position. This may allow the receptacle to project in the drum so as to collect a sample, but be at least partially retracted from the drum so as to reduce its influence on the movement of tablets, air or coating fluid therein (so as to improve the evenness of the coating and reduce the chances of tablets being damaged).

The housing may comprise a releasable attachment feature for removably mounting the tablet sampler assembly to a tablet coating machine.

The housing may be configured to be removably mounted to a tablet coating machine via mutually interlockable lugs or threads, by a tri-clover mechanism, or in any other suitable fashion. The tablet sampler assembly being removably mountable to a coating machine may enable easier inspection, cleaning and/or repair of the tablet sampler assembly and/or the coating machine. It may also enable faster changeovers between batches in a tablet coating machine. For instance, the machine may be run with one sampler assembly in place and another in a ready state, so that at a changeover, the other sampler assembly can be installed and used straight away, allowing the sampler assembly previously used to be cleaned at leisure. Alternatively, cleaning of the sampler assembly may be incorporated into the cleaning regime of the coating machine.

Said portion of the receptacle which is movable between the collecting and non-collecting positions may be formed by substantially the entire receptacle, the receptacle thereby being movable between said positions by movement relative to the housing. This may allow the sample contained within the receptacle to be moved, for instance so as to be removed from the tablet sampler assembly for testing, with advantageous ease and simplicity.

Alternatively, less than substantially all the receptacle may be movable. For instance, the receptacle may have a cavity for containing tablets, the cavity being fixed relative to the housing, and a lid portion (being the said portion) which is movable between said positions to cover or uncover the cavity.

The receptacle may be movable between the collecting and non-collecting positions via rotational movement relative to the housing. Alternatively, or in addition, the receptacle may be movable between the collecting and non-collecting positions via linear movement relative to the housing.

The receptacle may be rotatable about and/or movable along an axis which is aligned with that of rotation of the drum, or one which is positioned radially or tangentially relative to the drum, or one which is positioned in any other suitable orientation.

Where the receptacle is movable by rotation and linear movement, said linear movement may be provided by a linear actuator, and said rotational movement may be provided by a lead screw mechanism which acts to translate said linear movement into said rotational movement.

A lead screw mechanism may be considered to be any mechanism which translates rotary motion into linear motion. Examples of lead screw mechanisms include roller screw mechanisms and ball screw mechanisms. A linear actuator may be considered to be an any actuator which provides linear force or motion, such as a pneumatic piston, a hydraulic cylinder or a solenoid.

Use of a lead screw mechanism to provide the rotational movement may provide a more compact tablet sampler assembly, as no space for a rotary actuator is needed.

In a tablet sampler assembly which utilizes a lead screw mechanism:

the lead screw mechanism may comprise a rotatable shaft fixed to or integral with the receptacle, and a nut which is fixed such that it cannot rotate relative to the housing;

the shaft may define a longitudinal axis and have a helical formation on its outer periphery, and the nut may have a formation of complementary shape to the helical formation of the shaft, the shaft and nut may be arranged whereby operation of the linear actuator moves the shaft linearly along its axis and through the nut, thereby causing said linear movement of the receptacle; and the formations of the shaft and nut may engage one another so as to translate linear motion of the shaft relative to the nut into rotational movement of the shaft relative to the nut, thereby causing said rotational movement of the receptacle.

Where the receptacle is movable linearly, it may be reciprocally received within a cavity in the housing, and may project outwardly from the cavity at least when in the collecting position.

The cavity may have an enlarged portion positioned to provide a clearance to accommodate tablets projecting from the receptacle. This may allow tablets projecting from the receptacle to be moved with the receptacle within the cavity, thus avoiding possible damage caused by contacting a surface of the cavity. The enlarged portion may be the entire cavity.

The receptacle may comprise one or more angled surfaces configured to displace tablets projecting from the receptacle during movement of the receptacle from the collecting position towards the non-collecting position.

The angled surfaces causing displacement of these tablets may be so configured to avoid the tablets being damaged by being crushed between the receptacle and the cavity.

The angled surfaces may displace tablets fully into or onto the receptacle, and/or out of or off the receptacle.

The receptacle may comprise a recess for containing at least part of said sample, and further comprise an overflow recess configured to receive one or more tablets displaced from the recess during movement of the receptacle from the collecting position towards the non-collecting position.

Where the receptacle has one or more angled surfaces and also an overflow recess, the angled surfaces may be configured to displace tablets projecting from the recess such that they enter the overflow recess. As an alternative, the angled surfaces may displace tablets projecting from the recess such that they fall from the receptacle or are fully received within the cavity, and the overflow recess may accommodate tablets displaced from the recess by another surface (for instance a mouth of a cavity of the housing).

Beneficially, the receptacle may be configured to sealingly engage with the housing. The receptacle may sealingly engage when in the collecting position and/or in the non-collecting position, may be sealingly engaged with the housing throughout its range of movement, or may be configured to sealingly engage in any other suitable position. The receptacle may sealingly engage with the housing via an o-ring seal, wiper seal, labyrinth seal, or in any other suitable fashion.

According to a second aspect of the present invention there is provided a tablet coating machine comprising: a tablet sampler assembly according to the first aspect of the invention, and a rotatable drum for containing a bed of tablets being coated, the drum comprising a circumferential peripheral wall and two end walls.

The second aspect of the invention may provide a tablet coating machine which is advantageously simple, quiet and/or compact for the reasons given above. Such a coating machine may allow samples of tablets to be extracted in an advantageously safe and/or quiet fashion, and/or in a manner which has reduced impact on the movement of air, tablets or coating material within the drum, as outlined above.

The tablet coating machine may further comprise a sampling blade configured to direct tablets towards the receptacle when the at least a portion of the receptacle is in the collecting position and the drum is rotating.

Use of a sampling blade to direct tablets towards the receptacle may allow the receptacle to be positioned in a location of minimal impact on the movement of air, tablets and coating material within the drum, while still allowing the receptacle to reliably receive a sample of tablets from the tablet bed when desired.

The table coating machine may further comprise a drum chute positioned to direct, towards the receptacle, tablets leaving the sampling blade.

The sampling blade may or may not also be configured to direct tablets towards the receptacle when said portion is in the non-collecting position and/or when the drum is not rotating. Where substantially the entire receptacle is movable between the collecting and non-collecting positions, this movement may move the receptacle into and out of the path of tablets guided by the sampling blade.

The sampling blade may be mounted to the drum and rotatable therewith. For instance, it may be mounted to one of the end walls of the drum.

The drum may be provided with one or more unloading blades configured to direct tablets towards an aperture of the drum when the drum is rotating, and the sampling blade may be attached to at least one of the one or more unloading blades.

Where the drum is provided with a plurality of unloading blades, the sampling blade may be attached to or integral to one of these unloading blades, or more than one.

The sampling blade may be attached to said unloading blade(s) by virtue of being integrally formed therewith.

The sampling blade being rotatable with the drum may allow it to intermittently 'dip' into the tablet bed during rotation of the drum so as to collect samples without the need for any additional actuators and control systems beyond those required by the drum itself.

The sampling blade may be positioned at an angle of between 10 and 55 degrees from perpendicular to an end wall of the drum. Further, it may be positioned at an angle of between 20 and 45 degrees, for instance between 30 and 35 degrees, from perpendicular to an end wall of the drum.

This may be beneficial in ensuring that the sampling blade is at an angle that is sufficiently steep to retain tablets thereon by holding them against the end wall to which the sampling blade is mounted (thereby preventing them falling off), but also sufficiently shallow that tablets on the sampling blade which do not enter the receptacle gently drop off it back onto the tablet bed, rather than being forcibly 'ejected' towards and against the end wall of the drum or the door to the housing. The angle from perpendicular of a sampling blade which is curved/arcuate in longitudinal cross section may be considered to be the angle from perpendicular of a straight line which connects the blade's lateral edges.

The sampling blade may be positioned in the drum at an angle of between 5 and 40 degrees from the radial direction. Further, it may be positioned at an angle of between 15 and 30 degrees, for instance between 20 and 25 degrees, from the radial direction.

This may be beneficial in ensuring that the sampling blade is at an angle that is sufficiently steep to allow it to 'scoop' tablets out of the tablet bed without them simply sliding off its radially distal end again, but also sufficiently shallow that a sample of tablets collected by the blade do not fall from its radially proximal end until the drum has rotated sufficiently for the blade to be positioned to feed the receptacle. The angle from the radial direction of a sampling blade which is curved along its length may be considered to be the angle from the radial direction of a straight line which connects the blade's longitudinal ends.

The sampling blade may be configured so that when the drum is positioned with the sampling blade horizontal, a vertical plane containing a radially innermost corner of the sampling blade and the point at which the longitudinal axis of the drum intersects a front face of the drum, is positioned at an angle of between 0 and 40 degrees to the front face. Further, it may be configured so that said angle is between 10 and 30 degrees, for instance between 15 and 25 degrees.

The front face of the drum may be defined by an aperture.

The sampling blade may have a radially proximal end which is configured so that when the drum is positioned with the sampling blade horizontal, a vertical plane running parallel to the longitudinal axis of the sampling blade meets a vertical plane defined by the radially proximal end of the sampling blade at an angle of between 80 and 110 degrees. Further, it may be configured so that said angle is between 90 and 100 degrees, for instance between 93 and 97 degrees.

The position of the longitudinal axis of a sampling blade which is curved along its length may be considered to be the position of a straight line which connects the blade's longitudinal ends.

The tablet sampler assembly may be positioned such that the portion of the receptacle lies outside the space occupied by a tablet bed during coating when said portion is in the collecting position. This may allow samples to be extracted without the tablet bed contacting the receptacle, thereby preventing the receptacle from obstructing movement of tablets within the tablet bed, and from contacting tablets within the bed with sufficient force to break them.

The receptacle may be positioned vertically above or below, and/or horizontally to the front, back, and/or either side of the drum.

The tablet sampler assembly may also be positioned such that the portion of the receptacle is also outside the space occupied by a tablet bed when said portion is in the non-collecting position.

According to a third aspect of the invention there is provided a method of collecting a sample of tablets from a tablet coating machine according to the second aspect of the invention, the method comprising:

moving the at least a portion of the receptacle to the collecting position;

allowing the receptacle to collect a sample from the rotating drum; and moving the at least a portion of the receptacle to the non-collecting position.

The third aspect of the invention provides a method of collecting a sample which is advantageously simple, safe and quiet, as described above. The method furthermore ensures containment of the environment within the tablet coating machine, with no disruption to the coating process as the drum is able to continuously rotate, such that the tablets are evenly coated, during sampling.

According to a fourth aspect of the invention there is provided a method of coating tablets using a tablet coating machine according to the second aspect of the invention, the method comprising:

placing a bed of tablets to be coated into the drum of the machine;

rotating the drum and applying a coating substance to the bed of tablets; and collecting a sample using the method according to the third aspect of the invention.

The fourth aspect of the invention provides a method of coating tablets in which samples can be collected with reduced impact on the movement of coating material, tablets and/or air within the drum, and thus with reduced impact on the evenness of the coating layer as described above.

BRIEF DESCRIPTION OF THE DRAWINGS

A specific embodiment of the present invention will now be described, by way of non-limiting example only, with reference to the accompanying drawings in which.

DETAILED DESCRIPTION

Figure 1:
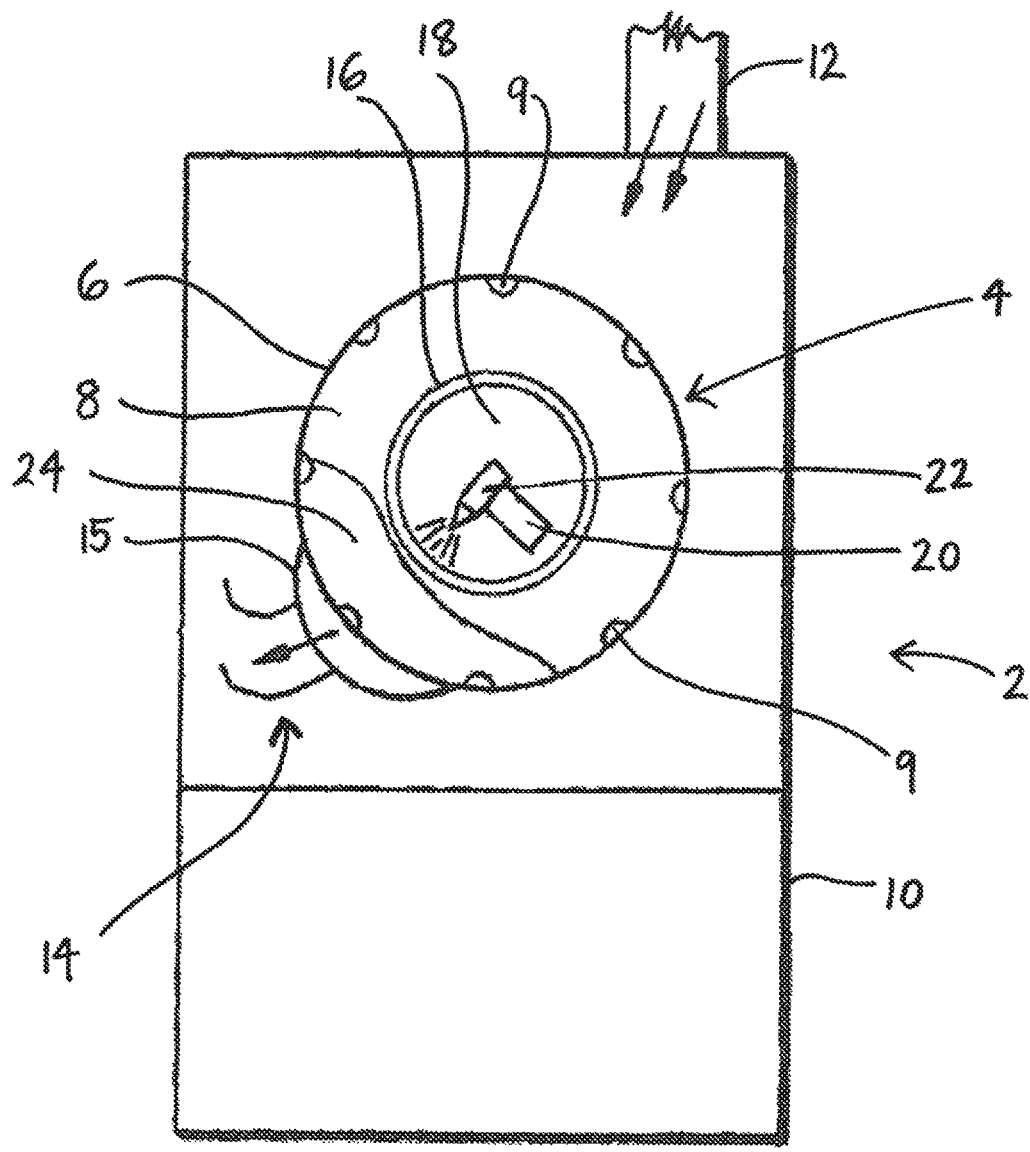
FIG. 1 is a schematic cross-sectional front view of a tablet coating machine according to a first embodiment of the invention.

FIG. 1 illustrates the basic construction of a tablet coating machine 2 according to a first embodiment of the invention. It has a drum 4, which is made up of a circumferential peripheral wall 6 and a pair of frustoconical end walls 8 (only one of which is visible in FIG. 1). The peripheral wall 6 of this embodiment is porous, and has a plurality of mixing baffles 9 on its inner surface. The drum 4 is rotatable within a casing 10. The casing has an air inlet 12, and a plenum 14 with a plenum cup 15, which is shaped to fit snugly against the exterior of the circumferential peripheral wall 6 of the drum 4. The drum 4 can be rotated about its axis within the casing by a drive mechanism (not shown), such as an electric motor, connected to the drum by a chain drive. The frustoconical end walls 8 each terminate in a circular aperture 16. On one end of the drum, typically the far end, this aperture is closed by a circular panel 18 which is integral to the drum and rotatable therewith. On the other end of the drum, typically the near end, this aperture in wall 8 of the drum 4 is closed by a door (not visible) of the casing 10. The portion of the machine 2 which includes the door is conventionally described as the 'front' of the machine. The coating machine 2 also has a spray arm 20 which projects rearwards from the door into the interior of the drum 4. Mounted on the spray arm 20 are one or more spray guns 22.

To coat a batch of tablets, the tablets are first loaded into the drum 4 through the door in the casing 10, forming a tablet bed 24. The drum 4 is then rotated continuously about its axis (clockwise from the perspective of FIG. 1), continuously mixing the tablet bed 24 with the aid of the mixing baffles 9. While the drum 4 rotates, the one or more spray guns 22 spray coating material (i.e. the material with which the tablets are to be coated, mixed with solvents and the like if required) onto the upper, exposed surface of the tablet bed 24. As the tablet bed 24 is continuously mixed, over time this action enables an even coating layer on the outer surface of each tablet to be provided.

While the drum 4 rotates, warm air is supplied to the casing 10 through the inlet 12 and suction is applied by the plenum 14 so that a continuous flow of warm air is produced. The plenum shoe 15 fits against the drum 4 with minimal clearance, and is positioned so that it is adjacent to the position of the tablet bed 24 while the drum is in motion. As such, the warm air sequentially flows through the inlet 12 into the casing 10 and from the casing 10 into the drum 4 (through the porous peripheral wall 6). From there, it passes from the drum 4, through the tablet bed 24, out of the drum (again through the peripheral wall 6) and into the plenum 14. Passing warm air through the tablet bed 24 in this fashion dries the coating material on the tablets and/or thermally cures the coating layer. Drying and/or curing may take place simultaneously with spraying, may take place afterwards, or drying/curing and spraying may take place alternately.

Figure 2:
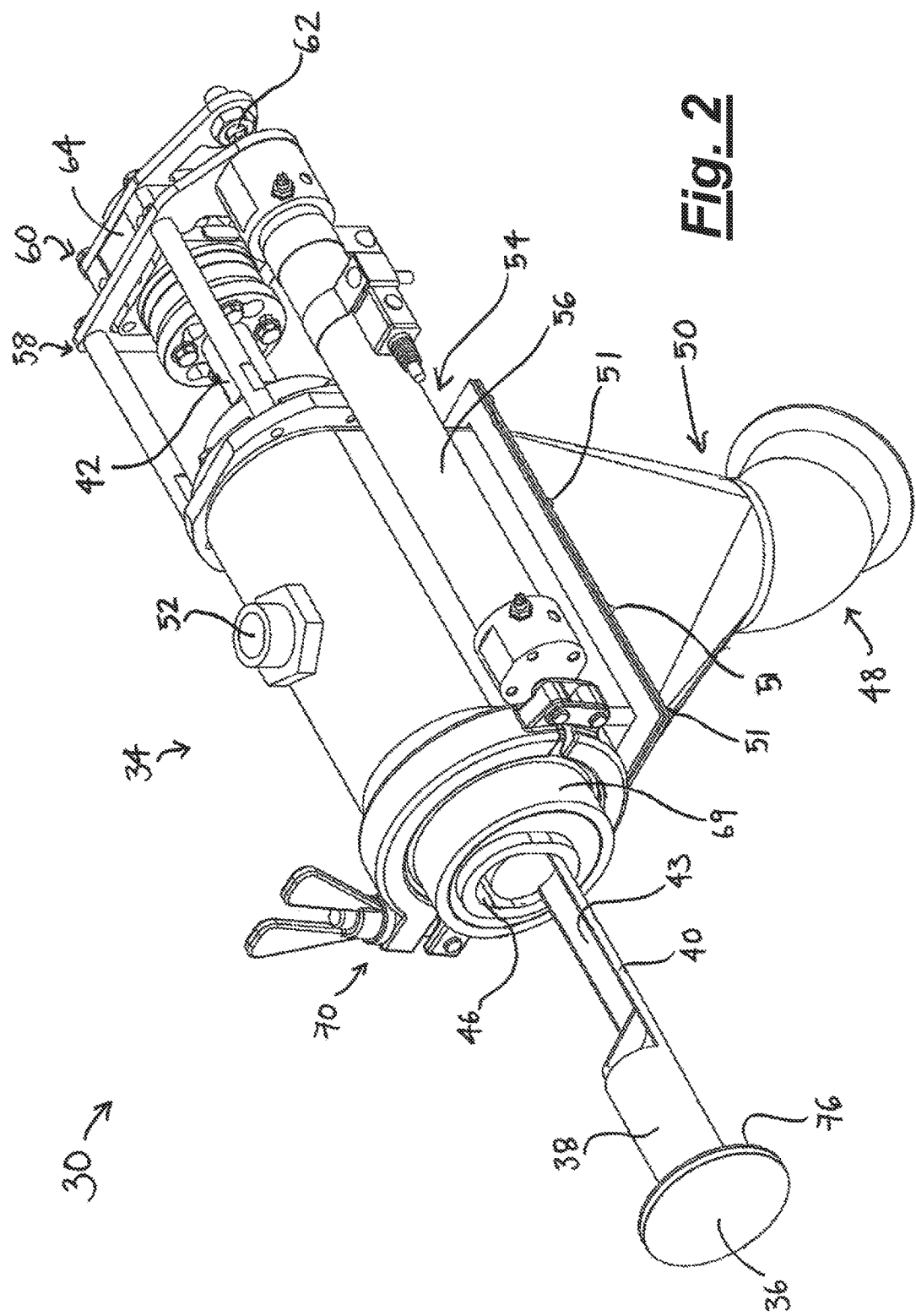
FIG. 2 is a perspective view of a tablet sampler assembly of the first embodiment.
Figure 3:
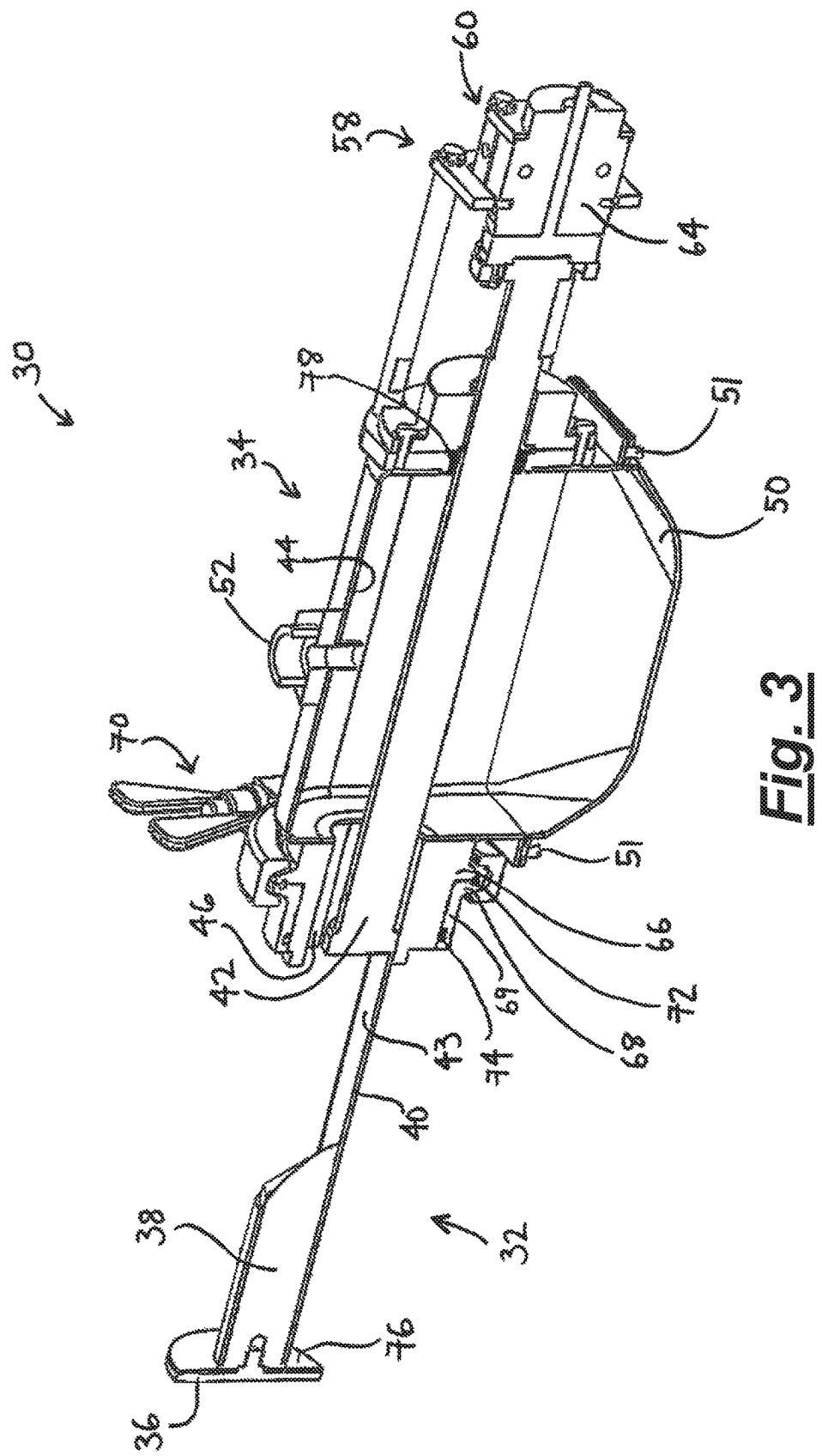
FIG. 3 is a cross-sectional perspective view of the tablet sampler assembly of FIG. 2, with a receptacle in a collecting position.

As discussed above, it is desirable to be able to extract samples from the tablet bed 24 in the drum 4 during the coating process, without interrupting rotation of the drum. FIGS. 2 and 3 show the tablet sampler assembly 30 of the first embodiment, which can be used for this purpose, in isolation. The sampler assembly 30 is shown in the configuration in which it would be when mounted to the tablet coating machine (2 in FIG. 1). The tablet sampler assembly 30 has a receptacle 32 and a housing 34. The receptacle 32 comprises an end cap 36, a distal shaft portion 38, a trough portion 40 and a proximal shaft portion 42. The trough portion 40 defines an arcuate recess 43 for receiving a sample of tablets, as discussed in more detail below.

The housing 34 has a cavity 44 within which the receptacle 32 is received. The cavity 44 has a mouth portion 46. The housing 34 also has an outlet port 48 positioned below the cavity 44 and connected thereto by a chute 50. The outlet port 48 takes the form of a tube with flange to which a container (not visible) with a complementary flange can be mounted using a tri-clover clamp (thereby forming a connection conforming to ISO 2852). Mounting a container to the outlet port 48 seals it, preventing the egress of matter contained within the cavity 44 (such as dust from tablets being coated in the drum of the machine to which the sampler assembly is mounted). The portion of the housing comprising the outlet port 48 and chute 50 is releasably connected to the part comprising the cavity 44 by bolts 51, allowing the two parts to be separated for cleaning. The housing 34 also has a wash port 52, through which cleaning fluid such as water can be injected.

The tablet sampler assembly 30 also has a linear actuator in the form of a pneumatic cylinder 54, the main body 56 of which is mounted to the housing 34 by a first actuator support structure 58. A second actuator support structure 60 is mounted to the output shaft 62 of the cylinder 54, and supports a rotary actuator in the form of a pneumatic motor 64. The pneumatic motor 64, in turn, is attached to the proximal shaft portion 42 of the receptacle 32.

FIGS. 2 and 3 also show the mechanism by which the tablet sampler assembly 30 can be mounted to the housing (10 in FIG. 1) of the tablet coating machine (2 in FIG. 1). The housing 34 has a flange 66, which can be connected to a complementary flange 68 on a connection piece 69 that is welded to the housing of the coating machine (not visible) by a tri-clover clamp 70. An o-ring seal 72 is positioned between the flanges 66, 68, allowing the connection between the tablet sampler assembly 30 and the coating machine 2 to be air-tight while still being selectively releasable. An additional seal 74 provides further protection from leaks.

FIGS. 2 and 3 show the tablet sampler assembly 30 with the receptacle 32 in a collecting position. The sampler assembly 30 is positioned on the coating machine (2 in FIG. 2) such that, with the receptacle 32 in the collecting position, it is in communication with the interior of the drum (4 in FIG. 1), projecting into the drum and enabling a sample of tablets therefrom to be received in the recess 43 of the trough portion 40. The mechanism by which the receptacle 32 receives the sample will be discussed below.

Figure 4:
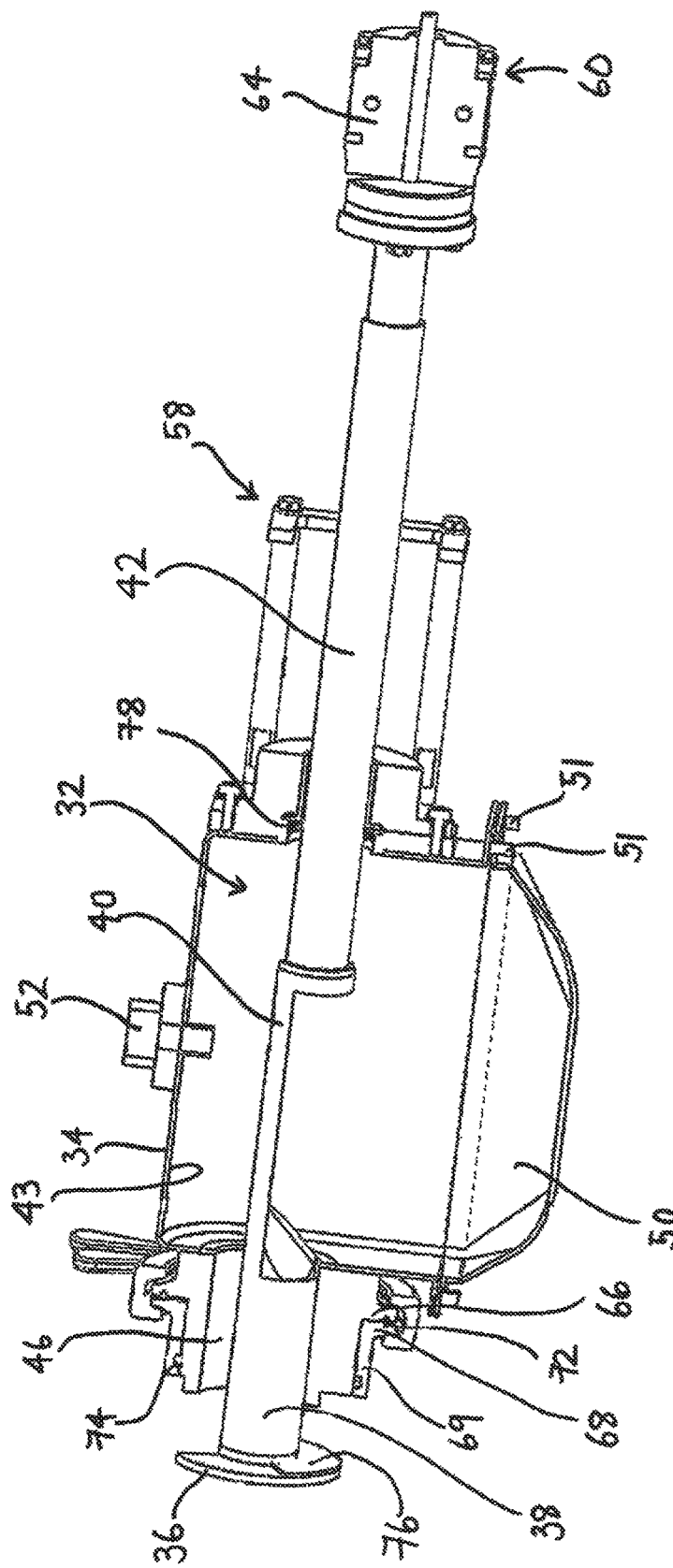
FIG. 4 is a cross-sectional perspective view of the tablet sampler assembly of FIG. 2, with a receptacle approaching a non-collecting position.

The receptacle 32 is movable relative to the housing from the collecting position to a non-collecting position, in which it is not in communication with the drum (and thus in which it cannot receive a sample of tablets therefrom). FIG. 4 shows the receptacle 32 in a position approaching the non-collecting position. As shown in FIG. 4, in combination with FIGS. 2 and 3, while in the collection position the receptacle projects from the mouth 46 of cavity 44. With the receptacle 32 in the non-collecting position, however, the end cap 36 contacts the mouth 46 and the receptacle 32 thus projects from the mouth 46 of the cavity 44 to only a minimal extent (however, as shown in FIGS. 3 and 4, the proximal shaft portion 42 of the receptacle 32 projects from the cavity 44 in the other direction at all times during normal use). In addition, with the receptacle 32 in the collecting position the recess 43 of the trough portion 40 faces upwards. In contrast, with the receptacle 32 in the non-collecting position the recess 43 faces downwards, as shown in FIG. 4.

As the recess 43 in the trough portion 40 faces downwards when the receptacle 32 is in the non-collecting position, with the receptacle in this position a sample of tablets in the recess can fall from the receptacle under gravity, whereupon they are directed by the chute 50 through the outlet port 48 and into a container (not visible) mounted thereto.

As described previously, it is important that tablet coating machines remain sealed from the external environment during coating, so as to prevent egress of potentially harmful substances. It is therefore important that the tablet sampling assembly 30 does not compromise this sealing. To that effect, the receptacle 32 is sealingly engageable with the housing 34. More particularly, a wiper seal 78 is disposed between the proximal shaft portion 42 of the receptacle 32 and the housing 34, and the end cap 36 of the receptacle 32 comprises an annular sealing pad 76. The wiper seal 78 prevents leakage of contaminants which enter the cavity 44 through the mouth 44; therefore, providing the outlet port 48 is also sealed, the housing (10 in FIG. 1) of the coating machine (2 in FIG. 1) is not compromised by the tablet sampler assembly 30. With the receptacle 32 in the non-collecting position, the sealing pad 76 is held against the mouth 46 of the cavity 44, sealing it shut. This prevents any contaminants (such as coating material, or dust from tablets being coated) from entering the cavity, allowing the outlet port 48 to be unsealed (i.e. by removing the container attached thereto so as to access the sample collected) without releasing contaminants to the environment. As such, the receptacle 32 and housing 34 remain sealingly engaged at all points during normal operation.

The linear movement of the receptacle 32 relative to the housing 34, which in this case is reciprocal movement of the receptacle (along its longitudinal axis) within the cavity 44, is controlled by the pneumatic cylinder 56. Extending the output shaft 62 of the cylinder 56 moves the second actuator support structure 60 away from the housing 34. As the second actuator support structure 60 is attached to the receptacle (by the pneumatic motor 64), this retracts the receptacle into the non-collecting position. Similarly, retracting the output shaft 62 of the cylinder 54 moves the second actuator support structure 60 towards the housing 34 and thus extends the receptacle towards the collecting position.

The rotational movement of the receptacle 32 relative to the housing 34, which in this case is rotation about the axis along which the receptacle is movable linearly, is controlled by the pneumatic motor 64. The second actuator support structure 60 is rotationally fixed, by virtue of it being mounted to the cylinder 54, therefore movement of the motor 64 rotates the receptacle 32 about its longitudinal axis. In this embodiment, the rotation of the receptacle 32 is timed so that it is complete before the receptacle reaches the non-collecting position (i.e. before the sealing pad 76 of end cap 36 contacts the mouth 46 of the cavity 44). This allows the motor 64 to be relatively small, as it does not need to supply sufficient force to overcome friction between the mouth 46 of the cavity 44 and sealing pad 76 of the end cap 36. It must merely overcome friction between the proximal shaft portion 42 and the wiper seal 78.

As shown more clearly in FIGS. 3 and 4, the portion of the mouth 46 of the cavity 44 which lies above the receptacle 32 (when the tablet sampler assembly 30 is in position on a tablet coating machine) is enlarged, providing a region of increased clearance with the receptacle. This region of increased clearance can accommodate tablets in the trough portion 40 which project upwards. If the mouth 46 was of circular cross section, matching the shaft portions 38, 42, any tablets projecting upwards from the trough portion 40 beyond the extremity of the shaft would be crushed during movement of the receptacle towards the non-collecting position.

Figure 5:
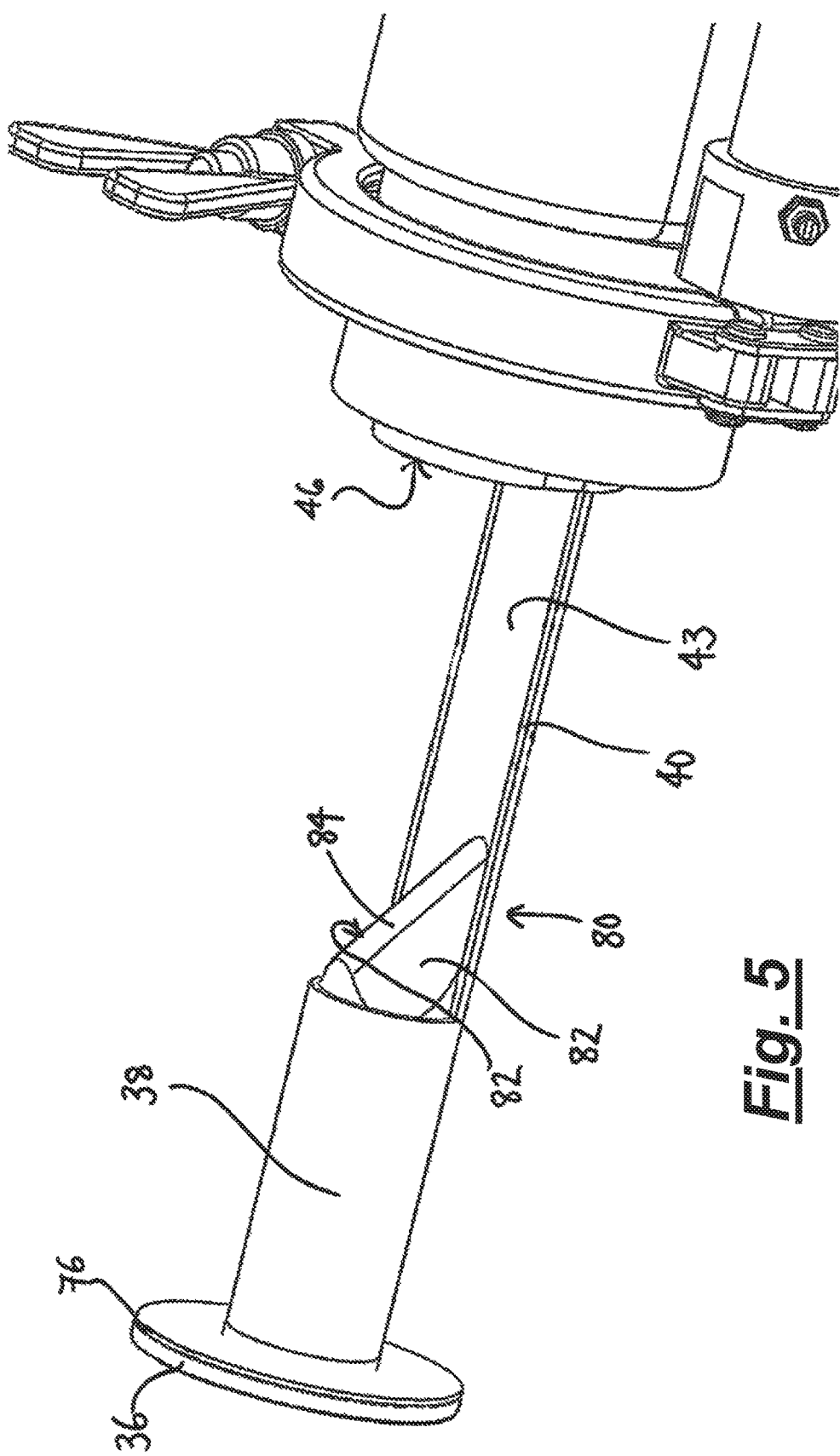
FIG. 5 is a perspective view of part of the receptacle shown in FIGS. 2 to 5.

An additional measure against damage to tablets during movement of the receptacle 32 towards the non-collecting position is shown in FIG. 5. The proximal end of the distal shaft portion 38 terminates in a plough structure 80, which comprises a pair of angled surfaces 82, which meet at a rounded junction 84. As the receptacle 32 moves towards the non-collecting position, tablets projecting sideways out of the trough portion 40 are directed off the trough portion by the angled surfaces 82, allowing them to return to the tablet bed rather than being crushed between the receptacle and the housing. The junction 84 between the angled surfaces 82 is rounded, so that there is no sharp edge between the surfaces which could damage tablets.

Figure 6:
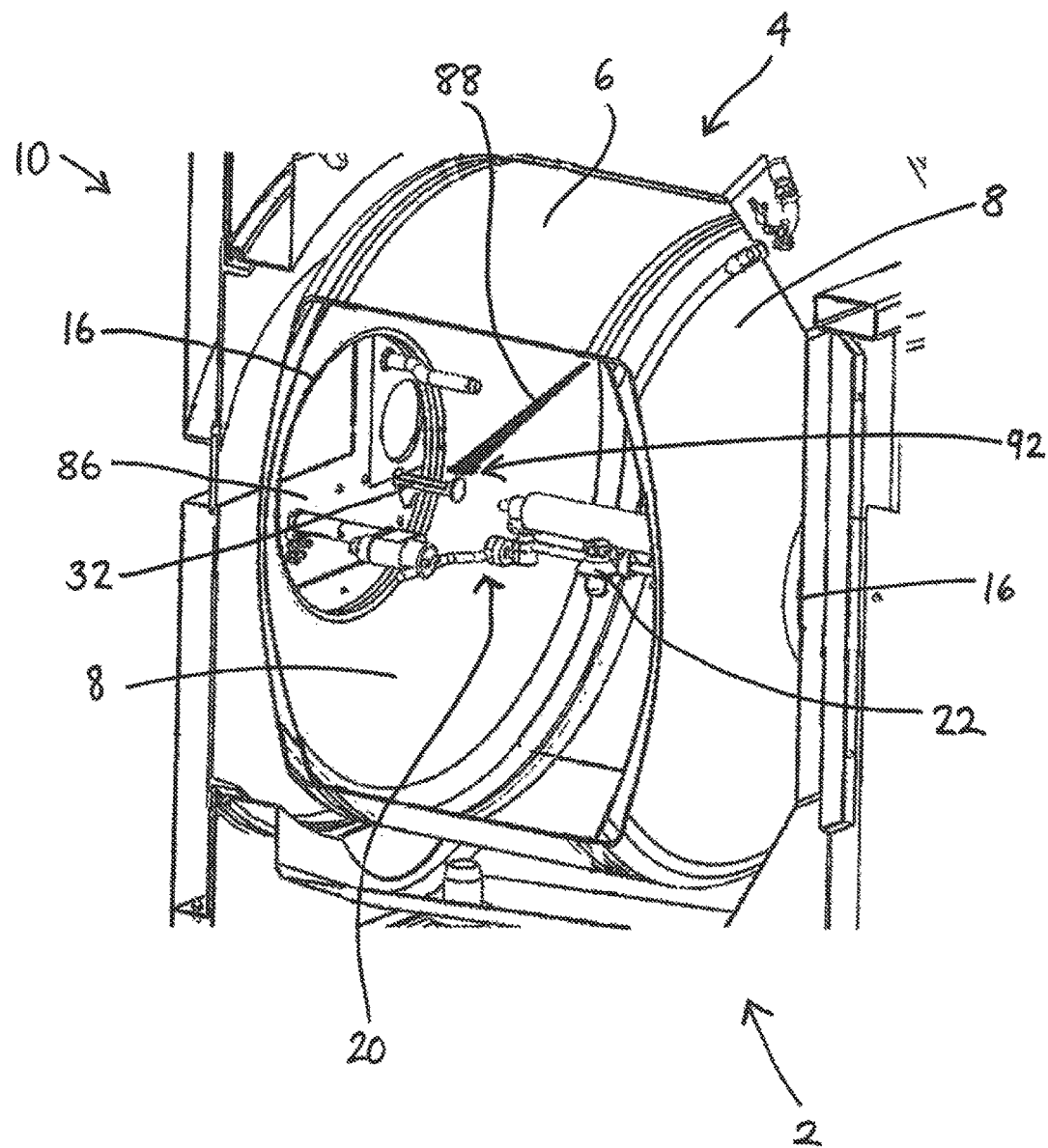
FIG. 6 is a cross-sectional perspective view of the side view of the tablet coating machine of the embodiment.
Figure 7:
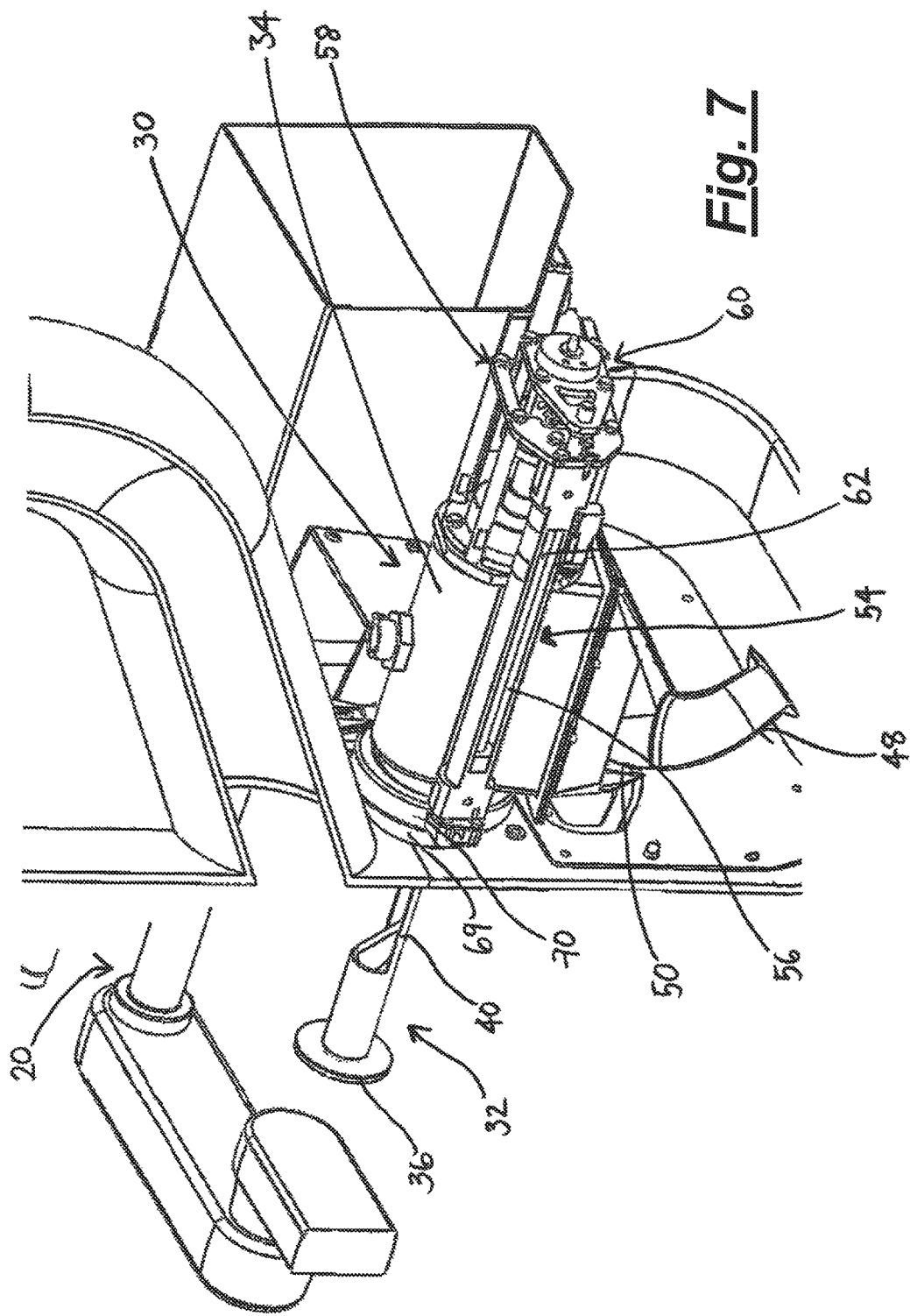
FIG. 7 is a cross-sectional perspective view of a portion of the tablet coating machine of the embodiment, from outside the drum.
Figure 8:
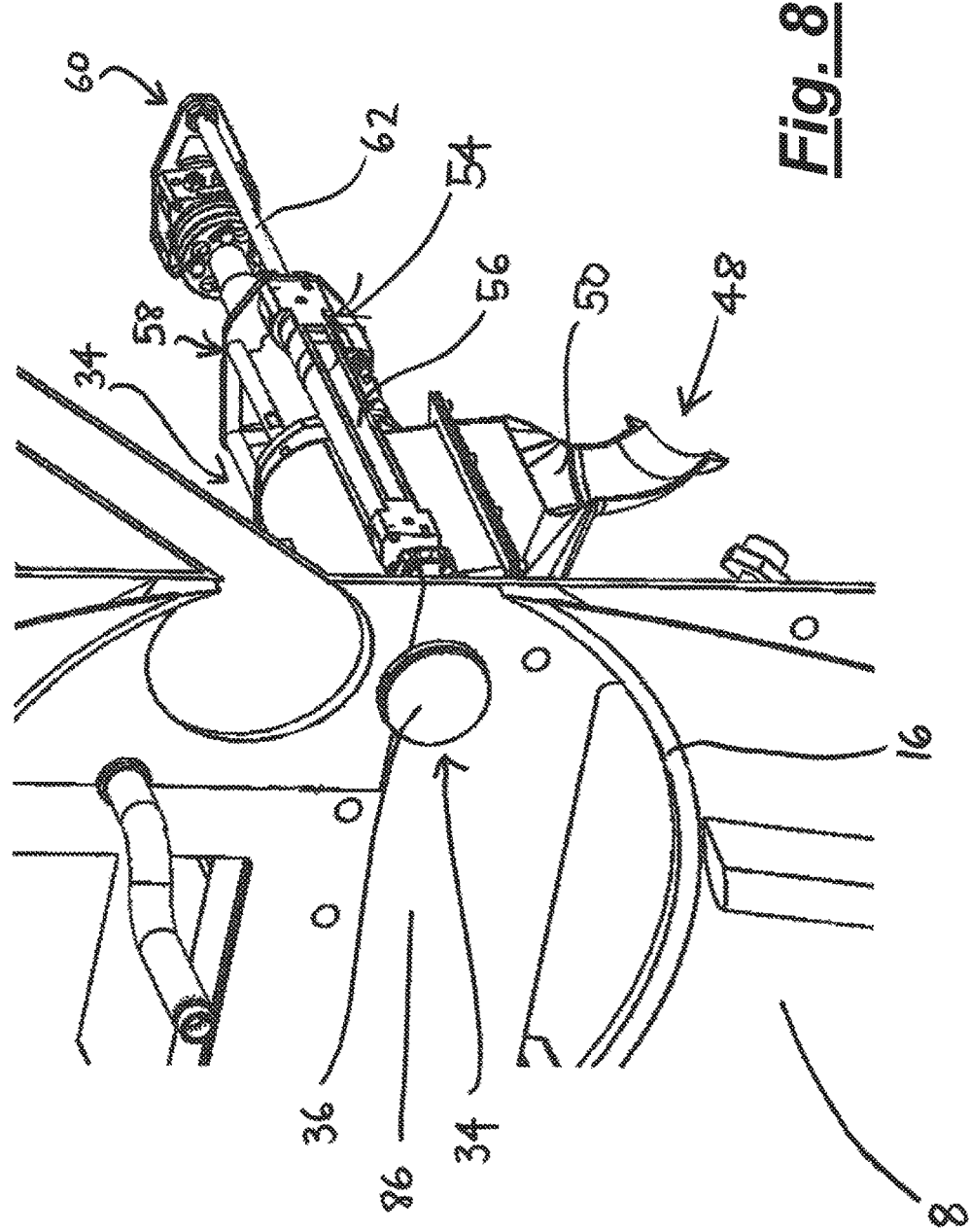
FIG. 8 is a cross-sectional perspective view of a portion of the tablet coating machine of the embodiment, from inside the drum.

FIGS. 6-8 show the tablet coating machine 2 with the tablet sampler assembly 30 in position. As described above, the casing 10 of the tablet coating machine 2 has a connection piece 69 welded to it, to which the housing 34 of the tablet sampler assembly 30 can be attached by a tri-clover clamp 70. This connection seals the sampler assembly 30 to the casing 10, preventing any leakage therebetween (and as described above, leakage from with the sampler assembly 30 is also prevented by seals).

During a tablet coating operation, the top of the tablet bed is conventionally around 40 mm away from the apertures 16 in the end walls 8. It is noteworthy that the tablet sampler assembly 30 is positioned so that the receptacle 32 is positioned within the area enclosed by the aperture 16 of the adjacent end wall 8. As such, at all times the receptacle 32 is positioned outside the space which may be occupied by the tablet bed. As such, there is little opportunity for tablets in the tablet bed to impact it and break.

As described above, with the receptacle 32 in the collecting position (as shown in FIGS. 6 and 7) it projects into the drum, and is in communication with the interior of the drum so as to receive a sample of tablets. More particularly, in this embodiment it projects through the door 86 in the casing 10, and into the drum 4 through the aperture 16 in the end wall 8 which is closed by the door.

FIG. 8 shows the receptacle 32 in the non-collecting position. As described above, with the receptacle 32 in the non-collecting position, the end cap 36 contacts the mouth of the cavity (not visible) of the housing 34. The housing 34 is positioned relative to the casing 10 such that the mouth of the cavity (not visible) lies flush with the inner surface of the door 86, so that with the receptacle 32 in the non-collecting position it projects into the drum 4 to a minimal extent. More particularly, it projects into the drum a distance equal to the thickness of the end cap 36. In this position, the receptacle 32 is out of communication with the interior of the drum (since the trough portion 40 is no longer accessible from the drum), and so no further tablets are removed from the drum.

As the receptacle 32 is positioned so as to remain outside the tablet bed, the drum 4 is provided with a sampling blade 88 (shown in FIG. 6) for directing tablets from the tablet bed towards the space occupied by the trough portion 40 of the receptacle (the portion which holds the sample tablets) when the receptacle is in the collecting position. The sampling blade is mounted to the end wall 8 of the drum 4 nearest the door 86 (and thus nearest the sampler assembly 30) and rotates with the drum. As the drum 4 rotates (in this case clockwise when viewed from the front), the radially outer end 90 of the sampling blade 88 is 'dipped' into the tablet bed. As the drum continues to rotate, the end 90 of the sampling blade 88 re-emerges from the tablet bed, but a sample of tablets remain supported on the blade 88. The blade 88 is angled towards the end wall 8 of the drum, preventing these tablets from falling off again. Continued rotation of the drum alters the angle of the sampling blade 88 and once the radially outer end 90 is higher than the radially inner end 92 (as shown in FIG. 6), tablets slide along the blade towards the inner end 92 before dropping off the blade and into the receptacle 32. When the receptacle 32 is in the non-collecting position, tablets simply slide off the inner end 92 of the sampling blade 88 and back into the tablet bed.

Figure 9:
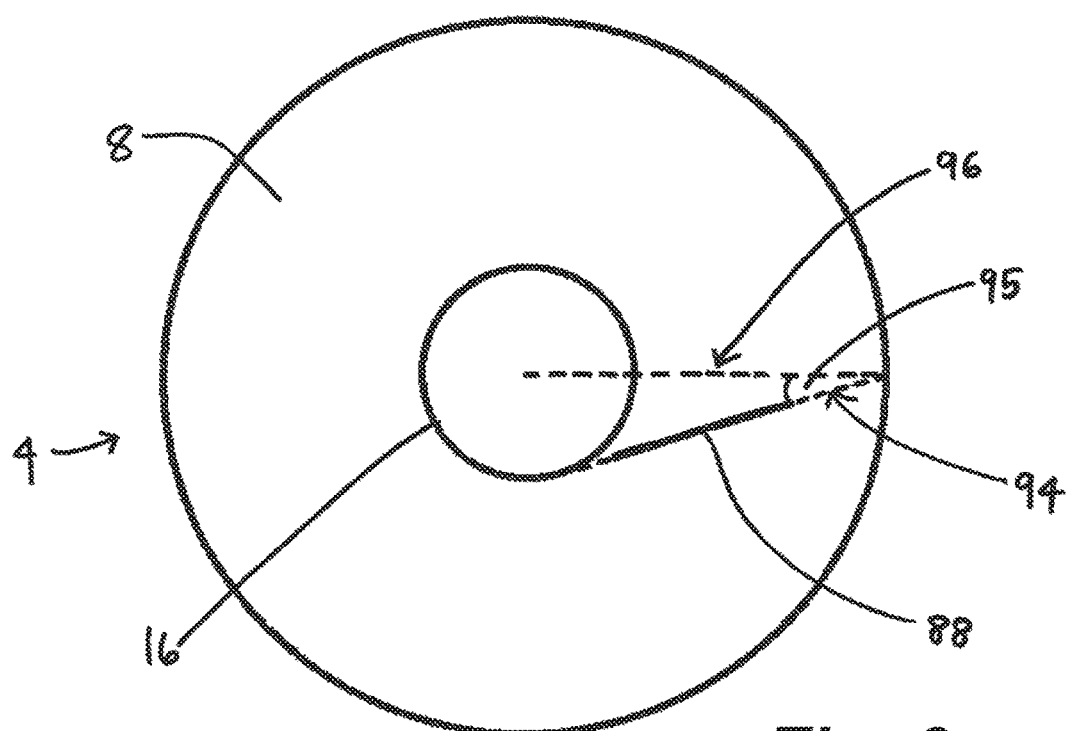
FIG. 9 is a schematic rear view of a drum of the coating machine of the embodiment.

The position of the sampling blade 88 may be altered according to the requirements of a particular sampling operation. In this exemplary embodiment the sampling blade 88 is positioned in the drum at an angle of around 22 degrees to the radial direction. In other words, as shown in FIG. 9 (not to scale), a line 94 defined by the sampling blade 88 and a radial line 96 which intersects line 94 at the perimeter of the drum 4 are positioned at an angle 95 of around 20 degrees to one another.

Figure 10:
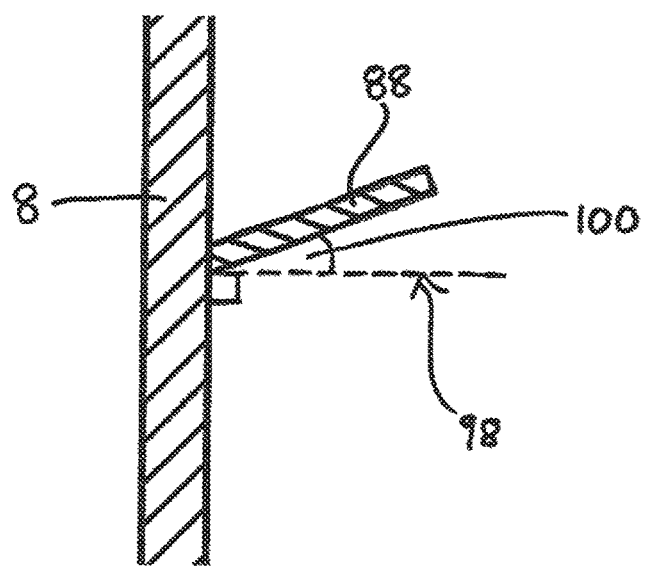
FIG. 10 is a schematic longitudinal cross section of a sampling blade of the drum, and the portion of the drum to which it is attached.

Further, in this embodiment the sampling blade 88 is positioned in the drum at an angle of around 25 degrees to an end wall 8 of the drum (in this case the end wall to which the sampling blade is mounted). In other words, as shown in FIG. 10 (not to scale), in longitudinal cross section the sampling blade 88, and a line 98 which is perpendicular to the end wall 8 and coterminous with the sampling blade 88, are positioned at an angle 100 of around 25 degrees to one another.

Figure 11:
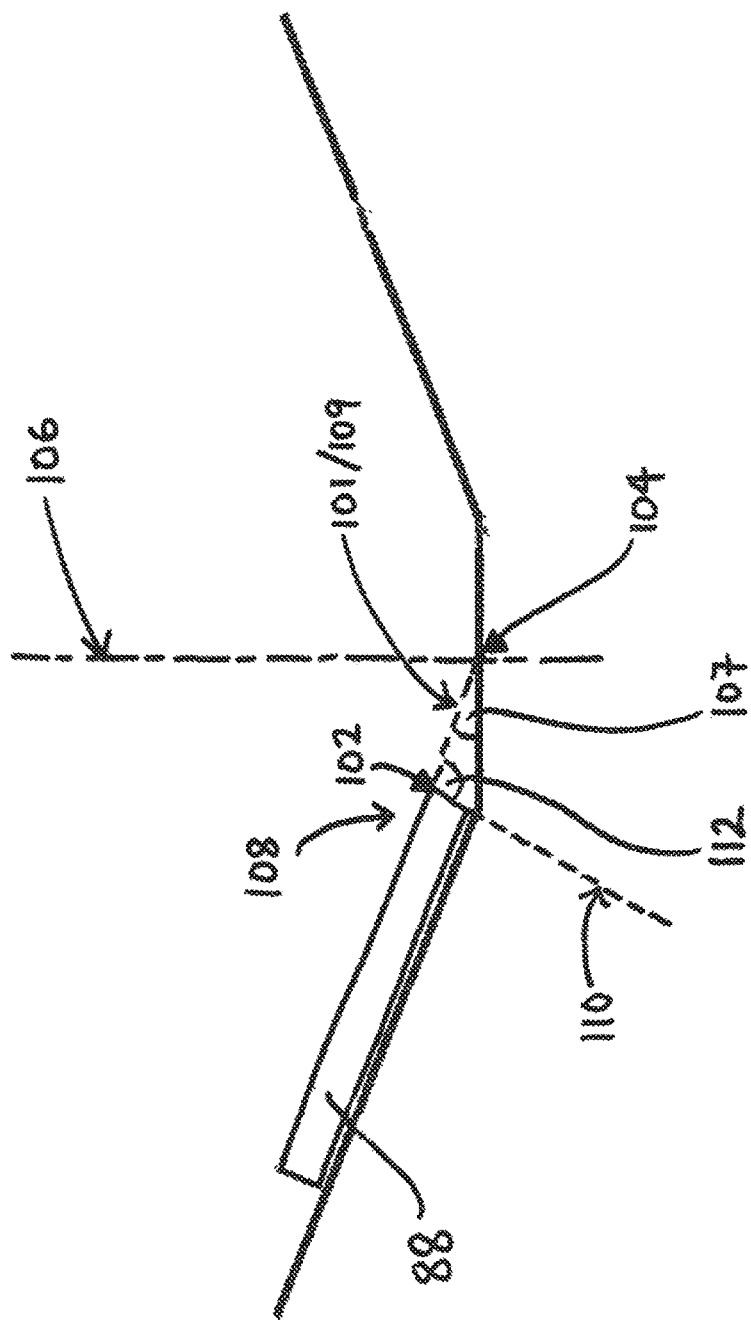
FIG. 11 is a schematic plan view of a portion of the drum of the coating machine of the embodiment.

FIG. 11 (not to scale) shows further detail on the position of the sampling blade 88 in this embodiment. When the drum is positioned so that the sampling blade 88 is horizontal, a vertical plane 101 containing the radially innermost corner 102 of the sampling blade and the point 104 at which the longitudinal axis 106 of the drum intersects the front face (which in this case is defined by the aperture 16) of the drum, is positioned at an angle 107 of around 20 degrees to the front face.

In addition, the radially proximal end 108 of the sampling blade 88 is swept back, rather than square. More particularly, when the drum is positioned so that the sampling blade is horizontal, a vertical plane 109 running parallel to the longitudinal axis of the sampling blade 88 meets a vertical plane 110 defined by the radially proximal end 108 of the sampling blade 88 at an angle 112 of around 95 degrees.

It is to be noted that although in this case the vertical plane 109 running parallel to the longitudinal axis of the sampling blade 88 is coplanar with the vertical plane 101 containing the radially innermost corner 102 of the sampling blade and the point 104 at which the longitudinal axis 106 of the drum intersects the front face, this should not be construed as limiting. Plane 109 may not necessarily intersect the radially innermost corner 102 and/or point 104. Similarly, plane 101 may not necessarily run parallel to the longitudinal axis of the sampling blade 88

During a coating operation (as described above) the receptacle is in the non-collecting position, and any tablets scooped up by the sampling blade 88 fall back into the tablet bed. When a sample is required, an operator inputs instructions to the coating machine's control panel (not visible). The receptacle 32 is then moved to the collecting position, where the trough portion receives tablets from the sampling blade. When the sample has been collected, the receptacle 32 is returned to the non-collecting position. In this embodiment the tablet coating machine 2 comprises a pair of sensors, one of which detects when the sampling blade 88 is approaching the position in which it will feed the receptacle 32, and the other of which detects when the sampling blade has passed this position. The movement of the receptacle 32 can therefore be coordinated with movement of the sampling blade 88, thereby preventing tablets being directed onto the receptacle while it is between the collecting and non-collecting positions. As described above, once the receptacle 32 reaches the non-collecting position, the tablets collected by the receptacle fall through the chute 50 and into a container (not visible) connected to the outlet port 48. The sample can then be removed for analysis.

In this embodiment one revolution of the sampling blade 88 is sufficient to collect a sample. However, in other embodiments multiple passes may be necessary so as to fill the receptacle to the required level. Similarly, though in this embodiment the receptacle is of sufficient size to hold a sample of the size required, this may not be the case (at which point the receptacle may be moved to the collecting position and back multiple times to collect a single sample). In some embodiments it may be desirable to produce a set of different sampling blades 88 and receptacles 32, allowing their capacities to be tailored to the sample size required. For instance, where particularly large tablets are to be coated, a larger receptacle 32 may be required. In addition, in some circumstances (such as if multiple passes of a sampling blade 88 are required so as to collect a sample of sufficient size) the drum 4 may be provided with two or more sampling blades.

Figure 12:
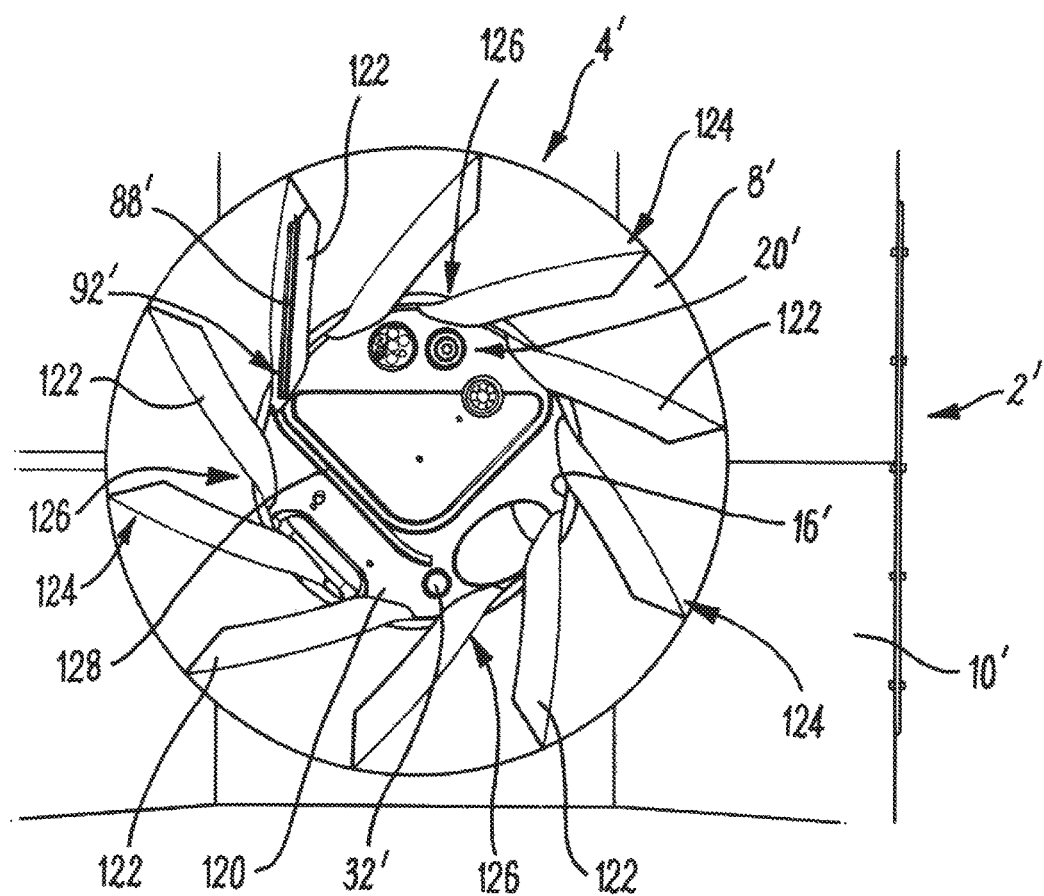
FIG. 12 is a side view of part of a tablet coating machine according to a second embodiment of the invention
Figure 13:
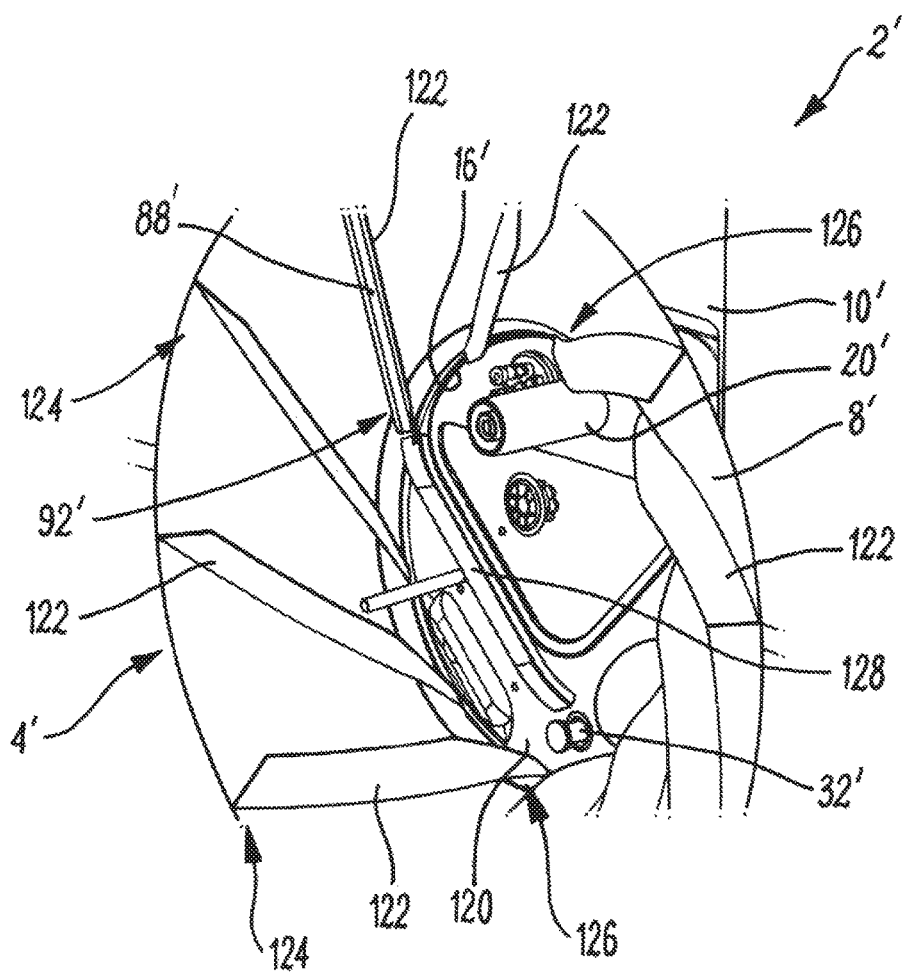
FIG. 13 is a perspective view of the part of the tablet coating machine shown in FIG. 12.
Figure 14:
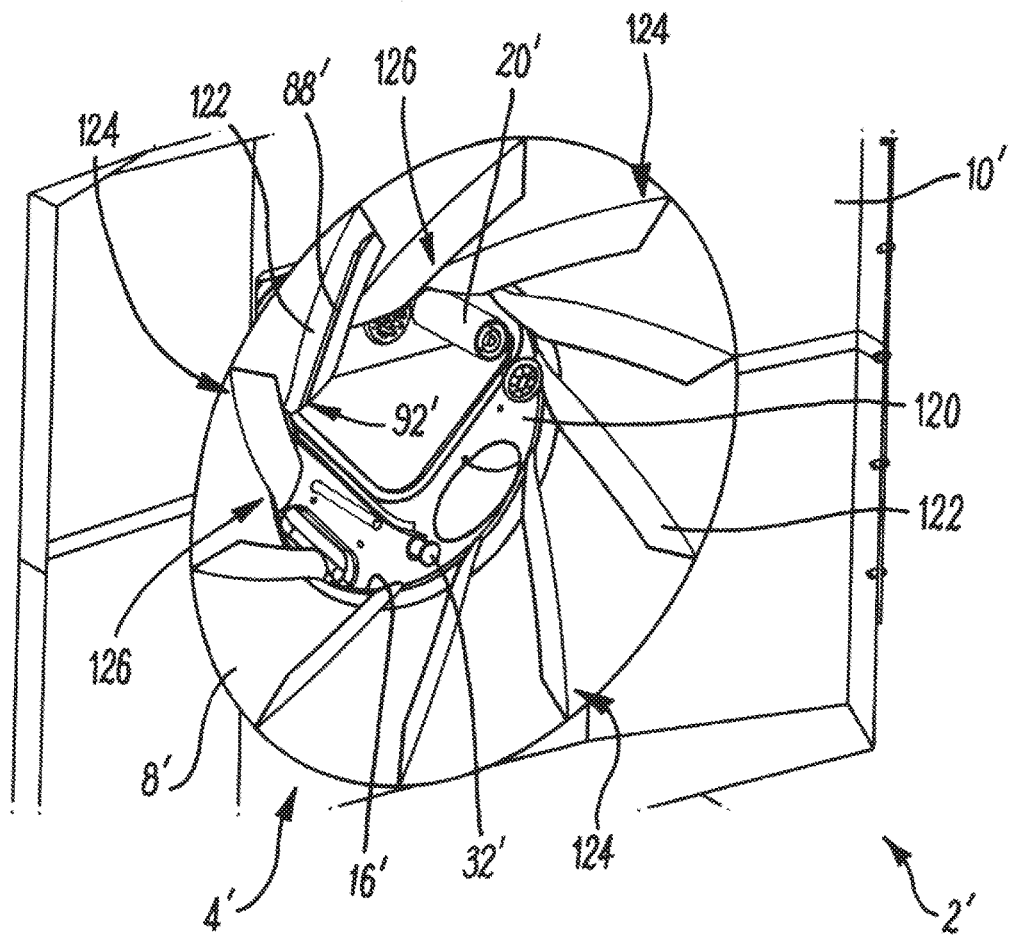
FIG. 14 is a perspective view of the part of the tablet coating machine shown in FIG. 12, from a different angle to that of FIG. 13.

A tablet coating machine 2' according to a second embodiment of the invention is shown in FIGS. 12 to 15. The machine of the second embodiment is similar to that of the first embodiment, therefore only the differences will be described here. FIGS. 12 to 14 show the frustoconical end wall 8' of the drum 4' which has an aperture 16' that is closed by a door 120 of the casing 10' (i.e. the 'front' end wall). The remainder of the drum 4' is not shown.

Unlike the first embodiment, in the second embodiment the front end wall 8' has an array of unloading blades 122. In this case the unloading blades 122 extend substantially the entire radial distance of the end wall 8'. The function of the unloading blades 122 is to assist with removal of tablets from the drum 4', through the aperture 16' and out of the door 120, once the coating process is complete. To unload the drum 4' it is rotated with the door 120 open (in this case anticlockwise from the perspective of FIGS. 12-14). The unloading blades 122 are configured such that as the drum 4' rotates, the radially outer end 124 of each unloading blade 122 'dips' into the tablet bed (not visible) when at the bottom of the drum. As the drum continues to rotate, that unloading blade 122 is lifted up from the tablet bed, and a quantity of tablets rests on top and is lifted up by it. Further rotation of the drum 4' causes the unloading blade 122 becomes angled so that its radially inner end 126 is lower than its radially outer end 124. At that point, the tablets resting on the unloading blade run radially inwards towards the inner end, and are then directed out of the aperture 16' by the unloading blade. The unloading blades 122 are therefore configured to operate in a similar manner to the sampling blade described above. That is, they utilize rotation of the drum to lift tablets from the tablet bed (not shown) and direct them towards a particular location.

In this case there are ten unloading blades 122, and the blades are arranged in a substantially evenly-spaced, substantially annular array around the axis of rotation of the drum 4. In other embodiments, however, there may be any other suitable number of unloading blades 122 (including a single unloading blade), and the unloading blades may be positioned in any other suitable configuration. For example, the unloading blades 122 may be unevenly distributed about the circumference of the drum 4' so that tablets exit the machine in 'pulses' as the drum rotates. Further, in this embodiment the unloading blades are positioned to direct tablets out of the aperture 16' when the drum 4' is rotating in the same direction as it rotates during the coating process, however in other embodiments the unloading blades may be positioned so that they assist with emptying the drum 4' when its direction of rotation is reversed. While in the first embodiment the sampling blade was attached directly to the end wall of the drum, in this embodiment the sampling blade 88' is attached to the end wall 8' of the drum 4' by virtue of being attached to one of the unloading blades 122. The sampling blade 88' of this embodiment works in the same manner as described in relation to the first embodiment, lifting tablets and directing them towards the receptacle.

As shown in FIG. 6, when the drum 4 of the first embodiment is in the position at which tablets fall from the sampling blade 88, the inner end 92 of the sampling blade is very close to the receptacle 32. Tablets therefore fall only a short distance from the sampling blade 88 into the receptacle 32, and are in little need of any further guidance. The same cannot be said of the second embodiment. Returning to FIGS. 12 to 14, in the case of the second embodiment when the drum 4' is in the position at which tablets fall from the sampling blade 88', the inner end 92' of the sampling blade is spaced apart from the receptacle 32' by a considerable distance, both vertically and horizontally. If no provision for tablets falling from the sampling blade 88' were provided, the tablets falling from such a height would stand a relatively high chance of breaking, and the horizontal distance between the sampling blade and receptacle 32' would mean that few tablets, if any, entered the receptacle.

On solution to this problem would be to move the position of the receptacle 32' (e.g. up and to the left from the perspective of FIGS. 12-14). However, this may not always be possible. For instance, in the case of the second embodiment fluid ducts and mechanical support for the spray arm 20' mean that the only space on the door 120 which is large enough to accommodate the sampler assembly is at the position shown. The second embodiment is therefore provided with a drum chute 128 which is mounted on the door 120 and which does not rotate. In this embodiment the drum chute 128 is elongate in shape and positioned at an incline to the horizontal, however in other embodiments it may take any other suitable shape and configuration. The chute 128 leads from the radially inner end 92' of the sampling blade 88' to the receptacle 32', and acts to guides tablets exiting the sampling blade so that they enter the receptacle. More particularly, the drum chute 128 conveys the tablets along the horizontal distance from the sampling blade 88' to the receptacle 32', and is positioned at an incline so that the tablets cover the vertical distance without picking up enough speed to expose them to any significant risk of breakage.

Figure 15:
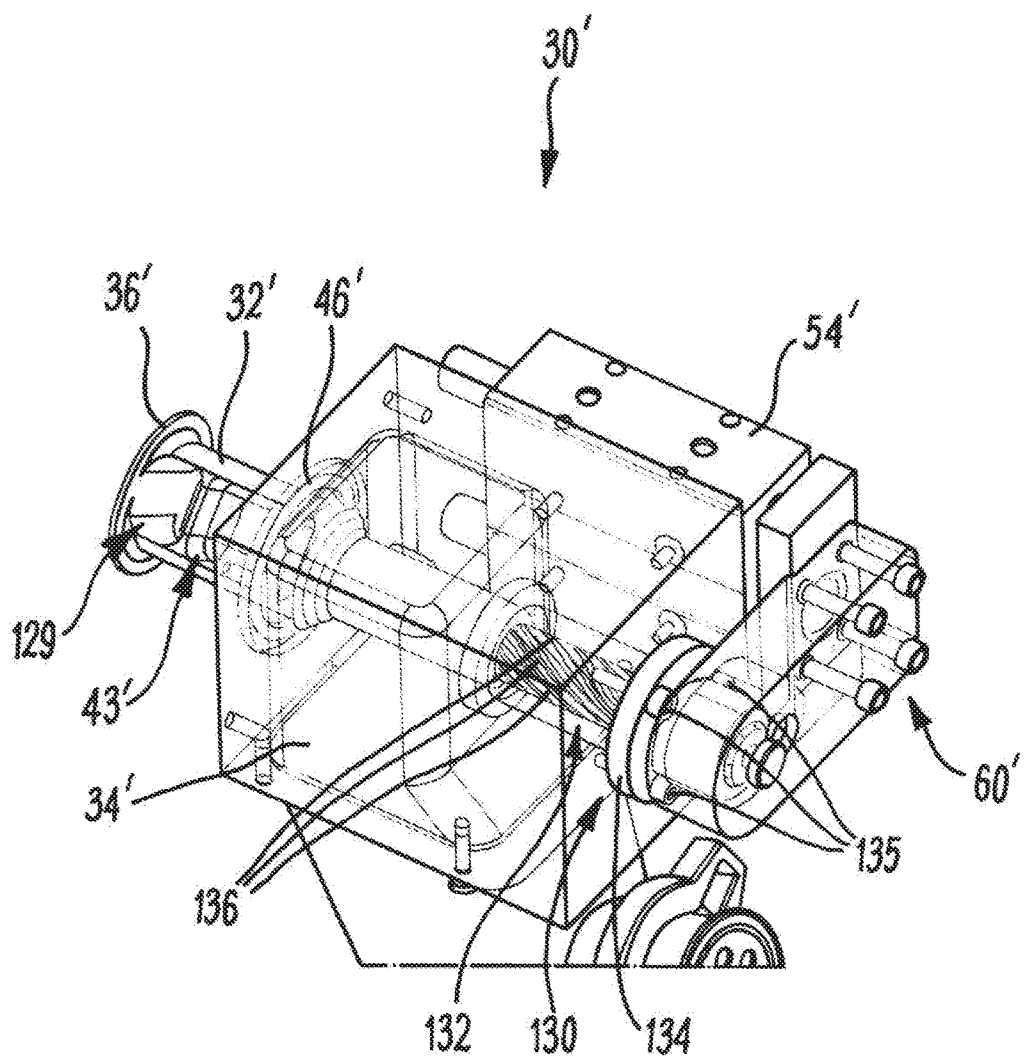
FIG. 15 is a perspective view of the tablet sampler assembly of the second embodiment of the invention.

FIG. 15 shows the sampler assembly 30' of the second embodiment of the invention. Like the sampler assembly of the first embodiment, in the second embodiment the sampler assembly 30' has a receptacle 32' which is movable relative to a housing 34' between a collecting position in which the receptacle is in communication with the interior of the drum, and a non-collecting position in which the receptacle is not in communication with the interior of the drum (FIG. 15 shows the receptacle 32' in the collecting position). As with the first embodiment, when the receptacle 32' is in the collecting position it projects from the housing 34' with its recess 43' upwards to collect tablets, and when the receptacle is in the non-collecting position it projects from housing to a minimal extent and its recess 43' faces downwards. Accordingly, as with the first embodiment, moving the receptacle 32' between the collecting and non-collecting positions requires the receptacle to move linearly and rotationally relative to the housing 34'.

The receptacle 32' of the second embodiment differs from that of the first embodiment in that it has an overflow recess 129. The coating machine is configured so that tablets from the drum enter the recess 43', with few or none entering the overflow recess 129. The overflow recess is therefore at least partially empty during normal use. The overflow recess 129 is positioned so that as the receptacle 32' is retracted towards the non-collecting position, any tablets in the recess 43' which project out from the recess are knocked into the overflow recess 129 by the mouth 46' of the housing. This prevents these tablets from being crushed between the mouth 46' of the housing and the end cap 36' of the receptacle 32' as discussed above. In this case any tablets in the overflow recess 129 are brought into the housing 34' when the receptacle is moved to the non-collecting position, and therefore form part of the sample. In other embodiments, however, some or all of the tablets in the overflow recess 129 may be removed before they can enter the housing 34' (for instance they may fall from the overflow recess 129 due to rotation of the receptacle 32' before the overflow recess enters the housing).

In the first embodiment linear movement of the receptacle was brought about by a linear actuator in the form of a pneumatic cylinder, and rotation of the receptacle was brought about by a rotational actuator in the form of a pneumatic motor. In the second embodiment, linear movement of the receptacle 32' is brought about by a pneumatic cylinder 54, but rotational movement is brought about by a lead screw mechanism 130. The lead screw mechanism 130 translates linear movement of the receptacle 32' relative to the housing 34' into rotational movement of the receptacle relative to the housing The lead screw mechanism 130 in this embodiment comprises a shaft 132 and a nut 134. The shaft 132 is fixed to the receptacle 32' so that any movement of the shaft (whether rotational or linear) causes corresponding movement of the receptacle. The shaft 132 is rotatably mounted to the support structure 60', meaning that the shaft 132 can move relative to the support structure 60', and therefore that the receptacle 32' can rotate relative to the housing 34'. The nut is fixed to the housing 34' (by bolts 135 in this case), so that it cannot rotate or move in any other direction relative to the housing.

The shaft 132 defines a longitudinal axis, has a set of formations in the form of helical ridges 136 positioned around its longitudinal axis. The shaft 132 therefore takes the form of an elongate helical gear. The nut 134 has an internal shape which is complementary to the external shape of the shaft 132. In this case, the nut 134 has a bore with a set of helical grooves (not visible). The helical grooves of the bore are of complementary shape to the helical ridges, and each groove of the nut accommodates one of the helical ridges of the shaft. The nut 134 therefore takes the form of an internally-threaded helical gear that is meshed with the shaft 132.

As with the first embodiment, to move the receptacle 32' to the non-collecting position, the pneumatic cylinder 54 is extended. Its output shaft (not visible) moves the second support structure 60' away from the housing, pulling the shaft 132 along its longitudinal axis (generally to the right from the perspective of FIG. 15), thereby retracting the receptacle 32'. As the shaft 132 moves backwards through the nut 134, the helical ridges 136 of the shaft must pass through their respective grooves in the bore of the nut 134. If the ridges 136 of the shaft 132 were straight then the shaft and nut would simply slide relative to one another. However, since the ridges 136 are helical, as the shaft 132 moves along its axis it is also forced to rotate about its axis. This rotation of the shaft 132 is transferred to the receptacle 32', therefore the receptacle rotates relative to the housing 34'. In this case the ridges 136 of the shaft 134 have a relatively large lead (i.e. the axial distance which would be covered by one 360 degree turn of the helix is relatively large). Accordingly, the amount of rotational movement produced per unit linear movement is relatively small. In this case, the shaft 134 rotates by around 180 degrees during travel between the collecting and non-collecting positions.

Although the lead screw mechanism above has been described in relation to the shaft having ridges and the nut having grooves, it may instead be considered that the shaft has grooves, and that the nut has internal ridges which project into these grooves. Furthermore, it is to be understood that the lead screw mechanism described above is merely one example, and that any suitable mechanism which can translate linear motion into rotary motion may be utilized. For instance, in a modification of the above embodiment the shaft may be substantially cylindrical but with have a single helical groove, and the bore in the nut may be substantially cylindrical but with a peg projecting into the groove in the shaft. As a further example, the shaft may take the form of a 'twisted' cuboid (i.e. a shape which is square in cross section, but where the angular position of that square changes along its length) and the nut may have a square hole. In this example, the corners and/or the faces of the twisted cuboid may be considered to be helical formations, the corresponding portion of the square hole being complementary to that formation.

It will be appreciated that numerous modifications to the above described design may be made without departing from the scope of the invention as defined by the appended claims. For instance, though the above embodiment utilizes pneumatic actuators, other embodiments may use hydraulic or electrical actuators, or may move the receptacle (or a portion thereof) by any other suitable means. For instance, the receptacle (or portion thereof) may be provided with a handle for manual manipulation. As another example, in other embodiments the plough structure may take any other suitable form. For instance, it may comprise a single angled surface.

For the avoidance of doubt, although the invention has been described in relation to a tablet coating machine, it is to be understood that reference to 'tablets' is intended to include any small object (typically, though not exclusively, with sizes in the range of 0.5 mm-30 mm) to which a coating is to be applied. For instance, the invention may also be applied to a machine for applying a sugar shell to chocolate beans, for applying a protective coating to pellets for medicament capsules, applying a layer such as pesticide to seeds (for instance for horticultural use), or a machine for applying lubricant, paint or the like to articles such as nuts and bolts. Similarly, the invention may be applied to machines other than coating machines, such as mixing machines.

While in the above embodiment the sample can be collected from the receptacle when (and only when) the receptacle is in the non-collection position, other embodiments may be configured to allow access to the receptacle at all times, or only when the receptacle (or part thereof) is in the collection position. In one example of the former arrangement, the receptacle may be in the form of a gravity slide which leads directly to a container which may be accessed at any time. In such a case, whether or not the receptacle was in the collecting position the sample in the container may be accessed.

Although in the second embodiment the sampling blade is positioned substantially parallel to the unloading blade to which it is attached, in other embodiments this may not be the case and the sampling blade may be positioned in any other suitable fashion. Further, although the second embodiment has a combination of unloading blades, a drum chute, an overflow recess and the sampling blade mounted to one of the unloading blades, it is to be understood that this should not be construed as limiting. For instance, a drum chute may be used in conjunction with a sampling blade which is not attached to an unloading blade. As another example, an overflow recess may be used whether or not unloading blades or a sampling blade (either mounted to an unloading blade or otherwise) are used. Similarly, the presence of unloading blades should not be construed as meaning that a sampling blade (where present) will necessarily be positioned thereon.

For the avoidance of doubt, the above references to the collecting and non-collecting positions of the receptacle should not be construed as limiting. Any position in which the receptacle is configured to be in communication with the interior of the drum may be considered to be a collecting position, and any position in which the receptacle is configured to be substantially out of communication with the interior of the drum may be considered to be a non-collecting position. For instance, though in the first embodiment the receptacle is described as being in the non-collecting position when the end cap is in contact with the mouth of the cavity of the housing, the position of the receptacle shown in FIG. 4 may instead be considered to be the non-collecting position.

The described and illustrated embodiments are to be considered as illustrative and not restrictive in character, it being understood that only preferred embodiments have been shown and described and that all changes and modifications that come within the scope of the invention as defined in the claims are desired to be protected. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary. Optional and/or preferred features as set out herein may be used either individually or in combination with each other where appropriate and particularly in the combinations as set out in the accompanying claims.

What is claimed is:

1. A tablet coating machine comprising:
   a rotatable drum for containing a bed of tablets being coated, the drum comprising a circumferential peripheral wall and two end walls;
   a tablet sampler assembly including:
      a housing attached to a portion of the tablet coating machine, and
      a receptacle for receiving a sample of tablets,
      wherein at least a portion of the receptacle is movable between a collecting position in which the receptacle is configured to be in communication with the interior of the drum, thereby enabling collection of a sample by the receptacle from the drum, and a non-collecting position in which the receptacle is configured to be substantially out of communication with the interior of the drum; and
   a sampling blade configured to direct tablets towards the receptacle when the at least a portion of the receptacle is in the collecting position and the drum is rotating.

2. The tablet coating machine according to claim 1 further comprising a drum chute positioned to direct, towards the receptacle, tablets leaving the sampling blade.

3. The tablet coating machine according to claim 1 wherein the sampling blade is mounted to the drum and rotatable therewith.

4. The tablet coating machine according to claim 3 wherein the sampling blade is mounted to one of the end walls of the drum.

5. The tablet coating machine according to claim 3 wherein the drum is provided with one or more unloading blades configured to direct tablets towards an aperture of the drum when the drum is rotating, and the sampling blade is attached to at least one of the one or more unloading blades.

6. The tablet coating machine according to claim 3 wherein the sampling blade is positioned at an angle of between 10 and 55 degrees from perpendicular to an end wall of the drum.

7. The tablet coating machine according to claim 3 wherein the sampling blade is positioned in the drum at an angle of between 5 and 40 degrees from a radial direction.

8. The coating machine according to claim 3 wherein the sampling blade is configured so that when the drum is positioned with the sampling blade horizontal, a vertical plane containing a radially innermost corner of the sampling blade and a point at which the longitudinal axis of the drum intersects a front face of the drum, is positioned at an angle of between 0 and 40 degrees to the front face.

9. The coating machine according to claim 3 wherein the sampling blade has a radially proximal end which is configured so that when the drum is positioned with the sampling blade horizontal, a vertical plane running parallel to the longitudinal axis of the sampling blade meets a vertical plane defined by the radially proximal end of the sampling blade at an angle of between 80 and 110 degrees.

10. A tablet coating machine comprising:
    a rotatable drum for containing a bed of tablets being coated, the drum comprising a circumferential peripheral wall and two end walls;
    a tablet sampler assembly including:
       a housing attached to a portion of the tablet coating machine, and
       a receptacle for receiving a sample of tablets,
       wherein at least a portion of the receptacle is movable between a collecting position in which the receptacle is configured to be in communication with the interior of the drum, thereby enabling collection of a sample by the receptacle from the drum, and a non-collecting position in which the receptacle is configured to be substantially out of communication with the interior of the drum;

wherein the tablet sampler assembly is positioned such that the portion of the receptacle lies outside a space occupied by a tablet bed during coating when said portion is in the collecting position.

11. A method of collecting a sample of tablets from a tablet coating machine according to claim 1, the method comprising:

moving the at least a portion of the receptacle to the collecting position;

allowing the receptacle to collect a sample from the rotating drum; and moving the at least a portion of the receptacle to the non-collecting position.

12. A method of coating tablets using a tablet coating machine according to claim 1, the method comprising:

placing a bed of tablets to be coated into the drum of the machine;

rotating the drum and applying a coating substance to the bed of tablets; and collecting a sample by:

moving the at least a portion of the receptacle to the collecting position;

allowing the receptacle to collect a sample from the rotating drum; and moving the at least a portion of the receptacle to the non-collecting position.

* * * * *